(12) United States Patent  
Gelikonov et al.

(10) Patent No.: US 8,159,677 B2
(45) Date of Patent: Apr. 17, 2012

(54) OPTICAL COHERENCE TOMOGRAPHY DEVICE AND METHOD HAVING IMPROVED BOUNDARY CONTROL AND DISTORTION CORRECTION

(75) Inventors: Valentin M. Gelikonov, Nizhny Novgorod (RU); Grigory V. Gelikonov, Nizhny Novgorod (RU); Felix I. Feldchtein, Framingham, MA (US)

(73) Assignee: Imalux Corporation, Cleveland, OH (US)

( * ) Notice: Subject to any disclaimer, the term of this patent is extended or adjusted under 35 U.S.C. 154(b) by 787 days.

(21) Appl. No.: 11/573,855

(22) PCT Filed: Aug. 4, 2005

(86) PCT No.: PCT/RU2005/000402
§ 371 (c)(1),
(2), (4) Date: Nov. 4, 2009

(87) PCT Pub. No.: WO2006/025759
PCT Pub. Date: Mar. 9, 2006

(65) Prior Publication Data
US 2010/0039651 A1 Feb. 18, 2010

(30) Foreign Application Priority Data

Aug. 18, 2004 (RU) .............................. 2004125427

(51) Int. Cl.
*G01B 9/02* (2006.01)

(52) U.S. Cl. ........................................................ 356/479
(58) Field of Classification Search .................. 356/479, 356/497; 250/227.19, 227.27; 600/476, 600/478
See application file for complete search history.

(56) References Cited

U.S. PATENT DOCUMENTS

| | | | | |
|---|---|---|---|---|
| 5,835,642 A * | 11/1998 | Gelikonov et al. | ................ | 385/4 |
| 5,867,268 A * | 2/1999 | Gelikonov et al. | ............ | 356/477 |
| 6,608,684 B1 * | 8/2003 | Gelikonov et al. | ............ | 356/479 |
| 6,950,692 B2 * | 9/2005 | Gelikonov et al. | ............ | 600/473 |

* cited by examiner

*Primary Examiner* — Michael A Lyons
(74) *Attorney, Agent, or Firm* — Renner, Otto, Boisselle & Sklar, LLP (57) ABSTRACT

Variants of an interferometric device are developed for examining internal structures of objects by means of optical coherence tomography, which allow for controlling a boundary location of the observation range. The device also allows for correcting a distortion of the tomographic image of the object under study, caused by lateral scanning, due to aberrations of the optical path length for the low-coherence optical radiation directed towards the object. Embodiments of the device include either one, or two fiber-optic controlled scanners, which in different combinations perform a function of in-depth scanning of the coherence window of low-coherence optical radiation within the observation range, a function of controlling a boundary location of the observation range, and a function of compensating the optical path length aberration for the low-coherence optical radiation directed towards the object, caused by lateral scanning.

21 Claims, 3 Drawing Sheets

OPTICAL COHERENCE TOMOGRAPHY DEVICE AND METHOD HAVING IMPROVED BOUNDARY CONTROL AND DISTORTION CORRECTION

CROSS REFERENCE TO RELATED APPLICATIONS

This application is a U.S. National Phase application which claims the benefit of priority of PCT Patent Application No. PCT/RU2005/000402, filed Aug. 4, 2005.

TECHNICAL FIELD

The present invention relates to devices for optical measurements and may be used in instruments for optical examination of the internal structure of objects, namely in low coherence reflectometers and optical coherence tomography devices which are applied, in particular, in medical diagnostics of individual organs and systems in a human body, including in vivo examinations, and in technical diagnostics, e.g., monitoring technological processes.

BACKGROUND ART

A virtue of interferometric devices used for examination of the internal structure of objects by means of low-coherence optical radiation, is a potential for obtaining images of turbid media with high spatial resolution, as well as performing non-invasive diagnostics in the course of medical examination, and non-destructive examination in the course of technical diagnostics of various equipment. Such devices are fairly well-known (e.g., by U.S. Pat. Nos. 5,321,501; 5,383,467; 5,459,570; 5,582,171; 6,134,003; and 6,657,727). The optical scheme of an interferometric device may be fully or partially implemented using bulk optical elements (U.S. Pat. No. 5,383,467), but more often such devices are designed using fiber-optic elements (U.S. Pat. Nos. 5,321,501; 5,459,570; 5,582,171; and 6,847,453).

Traditionally, such devices include a source of low coherence optical radiation, an optical interferometer and a delivering member for delivering low coherence optical radiation to the object under study. The optical interferometer includes at least one optical coupler and two arms. At least one of the arms of the optical interferometer includes a controlled scanner which performs in-depth scanning of the coherence window of low coherence optical radiation within the observation range. The controlled scanner is connected with a source of control voltage. The delivering member for delivering low-coherence optical radiation to the object under study may be part of one of the arms of the optical interferometer (e.g., U.S. Pat. No. 5,321,501; RU Patent No. 2100787), or may be placed outside the optical interferometer (e.g., U.S. Pat. No. 6,847,453). No matter where the delivering member for delivering low coherence optical radiation to the object under study is placed, the optical interferometer is usually implemented as a Michelson interferometer (e.g., U.S. Pat. Nos. 5,321,501; 5,459,570; 6,069,698; and 6,134,003; RU Patent No. 2100787; RU Patent No. 2148378; and RU Patent No. 2169347), or as a Mach-Zehnder interferometer (e.g., U.S. Pat. Nos. 5,582,171; and 6,687,010). Other known embodiments use optical interferometers of a hybrid type (e.g., U.S. Pat. Nos. 5,291,267; and 6,657,727).

In interferometric devices that employ the optical coherence tomography method, an interference signal is only registered, when the difference between optical lengths of the arms of the optical interferometer is within the coherence window dimension, which ranges from 5 to 20 micron. While examining an object, in-depth scanning of the object under study is achieved by scanning the coherence window within an observation range, which typically is up to ~2-5 mm. Thus, when designing an interferometric device according to any of the above optical schemes; special attention needs to be paid for matching optical lengths of the arms of the optical interferometer.

Matching between the optical arms of the optical interferometer is capable of being disrupted in the course of device operation, for example, as a result of replacing the optical probe, of unequal change in the optical lengths of the arms of the optical interferometer due to a thermal impact of the environment, of lateral scanning of objects with deep profiles, of moving the object under study or the lateral scanner. In addition, in the course of device operation, there may be a need to shift the observation range with a purpose of examining other parts of the object.

There is also known including an additional controlled scanner in one of the arms of the optical interferometer in order to control the location of a boundary of the observation range (e.g., U.S. Pat. Nos. 6,069,698; 6,191,862; 6,552,796; and 6,615,072).

A disadvantage of these devices is that the controlled scanners (both the controlled scanners performing in-depth scanning of the coherence window of low coherence optical radiation within the observation range, as well as the controlled scanners that perform changing of a boundary location of the observation range), are implemented as mechanical delay lines. While it is feasible to automate the measurement process, devices using such delay lines are expensive, fairly complicated, sensitive to vibration and environment conditions, and therefore are hardly suitable for medical examinations, especially in vivo studies.

Another shortcoming of known technical solutions, is their inability to correct distortion of the rendered tomographic image of the cross-section of the object under study in the case when the interferometric device is part of an optical coherence tomography device, wherein the lateral scanning device is, at least partially, part of the optical probe. This distortion is experienced due to aberrations in the optical path length for the low coherence optical radiation directed towards the object under study, caused by lateral scanning. The distortion becomes particularly obvious when an object with a flat surface is examined. As a result of this aberration, the rendered tomographic image of the cross-section of the object under study appears curved. The distortion of the tomographic image is associated with tomographic image rendering from an interference signal, the latter being a result of interference of optical radiation returning from the object under study and optical radiation passing along a reference path. For the lateral scanning method mentioned above, the low coherence optical radiation is directed towards the object under study from points which are located at different distances from the optical axis of the device. Thus, while the optical path length for the low coherence optical radiation propagating along a reference path is invariable, the optical path length for the low coherence optical radiation directed towards the object under study does not remain constant in the process of lateral scanning, which overall results in distortion of the rendered tomographic image.

The international application PCT/RU 2003/000252 (RU Patent No. 2242710) describes an interferometric device which provides correction of the tomographic image distortion by correcting the above-mentioned aberration with a specific lens system installed inside of the fiber-optic probe. However in some cases, for instance, for medical examinations the required dimensions of the fiber-optic probe are so diminutive that would impede introduction of such a lens system.

Two modifications of an interferometric device are known from RU Patent No. 2100787. One of them includes a source of low coherence optical radiation and an optical interferometer, which are optically coupled. The optical interferometer is implemented as a Michelson interferometer and includes an optical coupler, a sampling arm and a reference arm. The sampling arm includes a delivering member for delivering low coherence optical radiation to the object under study, which is designed an optical probe.

One of the arms of the optical interferometer includes a fiber-optic controlled scanner, which performs a function of in-depth scanning of a coherence window of the low-coherence optical radiation within an observation range of the object under study. The fiber-optic controlled scanner is designed as a fiber-optic piezoelectric controlled delay line which allows for varying the optical path length of a corresponding arm of the optical interferometer within at least several tens of operating wavelengths of the source of optical radiation. The fiber-optic controlled scanner includes a piezoelectric element characterized by a high transverse inverse piezoelectric effect and an optical fiber attached to the piezoelectric element. The piezoelectric element is capable of having an electric field produced within it. A dimension of the piezoelectric element in a direction generally orthogonal to the electric field vector substantially exceeds a dimension of the piezoelectric element in a direction generally aligned with the electric field vector. The length of the optical fiber substantially exceeds a diameter of the piezoelectric element. The fiber-optic controlled scanner is connected with a source of AC control voltage.

The second modification of the interferometric device known from RU Patent No. 2100787 also includes a source of low-coherence optical radiation and an optical interferometer, which are optically coupled. The optical interferometer is implemented as a Michelson interferometer and includes an optical coupler, a sampling arm and a reference arm. The sampling arm includes a delivering member for delivering low-coherence optical radiation to the object under study, which is designed an optical probe. Each arm of the optical interferometer includes a fiber-optic controlled scanner which performs a function of in-depth scanning of a coherence window of the low-coherence optical radiation within an observation range of the object under study. Each fiber-optic controlled scanner is designed as a fiber-optic piezoelectric controlled delay line. The piezoelectric fiber optic delay line allows for varying the optical path length of a corresponding arm of the optical interferometer within at least several tens of operating wavelengths of the source of optical radiation. The delay line includes a piezoelectric element characterized by a high transverse inverse piezoelectric effect and an optical fiber attached to the piezoelectric element. The piezoelectric element is capable of having an electric field produced within it. A dimension of the piezoelectric element in a direction generally orthogonal to the electric field vector substantially exceeds a dimension of the piezoelectric element in the direction generally aligned with the electric field vector. The length of the optical fiber substantially exceeds a diameter of the piezoelectric element. The optical interferometer further includes a source of AC control voltage connected with the fiber optic controlled scanner.

According to RU Patent No. 2100787, both modifications of the interferometric device may be used as part of a device for optical coherence tomography.

The interferometric devices known from RU Patent No. 2100787 share one major advantage—they may be implemented entirely fiber-optic without using expensive moving mechanical parts. This facilitates application of such devices in medical practice, since fiber-optic controlled scanners used in the devices do not require additional adjustment and calibration in the course of operation. However, the interferometric devices known from RU Patent No. 2100787, do not provide means for controlling a boundary location of the observation range. In addition, these devices do not allow for a distortion correction of the tomographic image of the cross-section of the object under study. The distortion is caused by the optical path length aberration for the low-coherence optical radiation directed towards the object under study. Such aberration occurs when an interferometric device is part of a device for optical coherence tomography, wherein the means for lateral scanning is, at least partially, part of the optical probe.

SUMMARY OF THE INVENTION

The object of this invention is to expand the class of interferometric devices intended for examining internal structures of objects using an optical coherence tomography method, allowing for controlling a boundary location of the observation range while simplifying operation of such devices. Another object of this invention is to expand the class of interferometric devices for optical coherence tomography, which allow for correcting a distortion of the tomographic image of the cross-section of the object under study, which distortion is caused by aberrations of the optical path length for the low-coherence optical radiation directed towards the object under study in the process of lateral scanning.

The first variant of the developed interferometric device the same as the first modification of the device known from RU Patent No. 2100787 includes a source of low-coherence optical radiation optically coupled with an optical interferometer, the latter being optically coupled with a delivering member for delivering low-coherence optical radiation to an object under study. The optical interferometer includes at least one optical coupler, two arms, and a fiber-optic controlled scanner which is located in one of the arms of the optical interferometer. The fiber-optic controlled scanner performs a function of in-depth scanning of a coherence window of the low-coherence optical radiation within an observation range of the object under study. The optical interferometer further includes a source of AC control voltage connected with the fiber-optic controlled scanner.

In contrast to the first modification of the interferometric device known from RU Patent No. 2100787, according to the invention, in the first variant of the developed interferometric device, the fiber-optic controlled scanner further performs a function of controlling a boundary location of the observation range. Besides, the optical interferometer further includes a source of DC control voltage connected with the fiber-optic controlled scanner.

In one particular embodiment, the delivering member for delivering low-coherence optical radiation is implemented as an optical probe.

In another particular embodiment, the interferometric device is part of a device for optical coherence tomography and includes means for lateral scanning which is, at least partially, part of the optical probe.

In another particular embodiment, the fiber-optic controlled scanner further performs a function of compensating an optical path length aberration for the low-coherence optical radiation directed towards the object under study, caused by lateral scanning. In this embodiment, the optical interferometer further includes a source of compensating control voltage, which is connected with the fiber-optic controlled scanner. The source of compensating control voltage is designed such as to allow for generating a control voltage that provides compensation of a deviation of a tomographic image of a cross-section of the object under study in the presence of the aberration, from an undistorted tomographic image of the cross-section of the object under study.

In another particular embodiment, the fiber-optic controlled scanner is implemented such as to allow for changing an optical length of a corresponding arm of the optical interferometer within at least several thousands of operating wavelengths of the source of optical radiation.

In a specific embodiment, the fiber-optic controlled scanner is designed as a piezoelectric fiber-optic controlled delay line.

It is advisable for the piezoelectric fiber-optic controlled delay line to include a piezoelectric element characterized by a high transverse inverse piezoelectric effect and an optical fiber attached to the piezoelectric element. In this embodiment, the piezoelectric element is capable of having an electric field produced within it. A dimension of the piezoelectric element in a direction generally orthogonal to the electric field vector substantially exceeds a dimension of the piezoelectric element in a direction generally aligned with the electric field vector. The length of the optical fiber substantially exceeds a diameter of the piezoelectric element.

In a particular embodiment, the piezoelectric element includes at least one piezoelectric plate.

In another particular embodiment, the optical fiber is attached to at least one surface of the at least one piezoelectric plate.

In another particular embodiment, the optical fiber is laid spirally.

In another particular embodiment, the spiral laying has multiple layers.

In another particular embodiment, the piezoelectric element is provided with electrodes.

In another specific embodiment, the fiber-optic controlled scanner is designed as a magnetostrictive fiber-optic controlled delay line.

In a particular embodiment, the delivering member for delivering low-coherence optical radiation to the object under study is part of one of the arms of the optical interferometer.

In another particular embodiment, the delivering member for delivering low-coherence optical radiation to the object under study is placed outside the optical interferometer and is optically coupled with it through an optical isolator. In this embodiment, the distal part of the delivering member for delivering low-coherence optical radiation to the object under study, together with the object under study form an additional optical interferometer.

In a specific embodiment, the optical isolator is implemented as an optical coupler.

In another specific embodiment, the optical isolator is implemented as an optical circulator.

The second variant of the developed interferometric device the same as an other realization of the first modification of the device known from RU Patent No. 2100787, is part of a device for optical coherence tomography. This device includes optically coupled, a source of low-coherence optical radiation, an optical interferometer, a delivering member for delivering low-coherence optical radiation to an object under study, designed as an optical probe, and means for lateral scanning, which is, at least partially, part of the optical probe. The optical interferometer includes at least one optical coupler, two arms, and a fiber-optic controlled scanner, which is located in one of the arms of the optical interferometer. The fiber-optic controlled scanner performs a function of in-depth scanning of a coherence window of the low-coherence optical radiation within an observation range of the object under study. The interferometric device further includes a source of AC control voltage connected with the fiber-optic controlled scanner.

In contrast to this realization of the first modification of the interferometric device known from RU Patent No. 2100787, according to the invention, in the second variant of the developed interferometric device, the fiber-optic controlled scanner further performs a function of compensating an optical path length aberration for the low-coherence optical radiation directed towards the object under study, caused by lateral scanning. Besides, the optical interferometer includes a source of compensating control voltage connected with the fiber-optic controlled scanner. The source of compensating control voltage is designed such as to allow for generating a control voltage that provides compensation of a deviation of a tomographic image of a cross-section of the object under study in the presence of the aberration, from an undistorted tomographic image of the cross-section of the object under study.

In a particular embodiment, the fiber-optic controlled scanner is implemented such as to allow for varying an optical length of a corresponding arm of the optical interferometer within at least several tens of operating wavelengths of the source of optical radiation.

In a specific embodiment, the fiber-optic controlled scanner is designed as a piezoelectric fiber-optic controlled delay line.

It is advisable for the piezoelectric fiber-optic controlled delay line to include a piezoelectric element characterized by a high transverse inverse piezoelectric effect and an optical fiber attached to the piezoelectric element. Moreover, the piezoelectric element is capable of having an electric field produced within it. A dimension of the piezoelectric element in a direction generally orthogonal to the electric field vector substantially exceeds a dimension of the piezoelectric element in a direction generally aligned with the electric field vector. The length of the optical fiber substantially exceeds a diameter of the piezoelectric element.

In another specific embodiment, the fiber-optic controlled scanner is designed as a magnetostrictive fiber-optic controlled delay line.

The third variant of the developed interferometric device, as well as the second modification of the device known from RU Patent 2100787, includes a source of low-coherence optical radiation, an optical interferometer and a delivering member for delivering low-coherence optical radiation to an object under study, which are optically coupled. The optical interferometer includes at least one optical coupler, two arms, a first fiber-optic controlled scanner, and a second fiber-optic controlled scanner. The optical interferometer further includes a source of AC control voltage connected with the first fiber-optic controlled scanner. The first fiber-optic controlled scanner performs a function of in-depth scanning of a coherence window of the low-coherence optical radiation within an observation range of the object under study.

In contrast to the second modification of the interferometric device known from RU Patent No. 2100787, according to the invention, in the third variant of the developed interferometric device, the second fiber-optic controlled scanner performs a function of controlling the location of a boundary of the observation range. In this variant, the optical interferometer further includes a controlled source of DC control voltage connected with the second fiber optic controlled scanner.

In a particular embodiment, the delivering member for delivering low-coherence optical radiation to the object under study is designed as an optical probe.

In another particular embodiment, the interferometric device is part of a device for optical coherence tomography, and includes means for lateral scanning which is, at least partially, part of the optical probe.

In another particular embodiment, one of the first fiber-optic controlled scanner, and the second fiber-optic controlled scanner, further performs a function of compensating an optical path length aberration for the low-coherence optical radiation directed towards the object under study, caused by lateral scanning. The optical interferometer further includes a source of compensating control voltage connected with a corresponding fiber-optic controlled scanner. The source of compensating control voltage is designed such as to allow for generating a control voltage that provides compensation of a deviation of a tomographic image of a cross-section of the object under study in the presence of the aberration, from an undistorted tomographic image of the cross-section of the object under study.

In another particular embodiment, the first fiber-optic controlled scanner is implemented such as to allow for varying an optical length of a corresponding arm of the optical interferometer within at least several tens of operating wavelengths of the source of optical radiation. The second fiber-optic controlled scanner is implemented such as to allow for changing an optical length of a corresponding arm of the optical interferometer within at least several thousands of operating wavelengths of the source of optical radiation.

In a specific embodiment, the first fiber-optic controlled scanner is designed as a piezoelectric fiber-optic controlled delay line.

In another specific embodiment, the second fiber-optic controlled scanner is designed as a piezoelectric fiber-optic controlled delay line.

It is advisable for the piezoelectric fiber-optic controlled delay line to include a piezoelectric element characterized by a high transverse inverse piezoelectric effect and an optical fiber attached to the piezoelectric element. Moreover, the piezoelectric element is capable of having an electric field produced within it. A dimension of the piezoelectric element in a direction generally orthogonal to the electric field vector substantially exceeds a dimension of the piezoelectric element in a direction generally aligned with the electric field vector. The length of the optical fiber substantially exceeds a diameter of the piezoelectric element.

In another specific embodiment, the first fiber-optic controlled scanner is designed as a magnetostrictive fiber-optic controlled delay line.

In another specific embodiment, the second fiber-optic controlled scanner is designed as a magnetostrictive fiber-optic controlled delay line.

In another particular embodiment, the delivering member for delivering low-coherence optical radiation to the object under study is part of one of the arms of the optical interferometer.

In another particular embodiment, the delivering member for delivering low-coherence optical radiation to the object under study is placed outside the optical interferometer and is optically coupled with it through an optical isolator. A distal part of the delivering member for delivering low-coherence optical radiation to the object under study together with the object under study forms an additional optical interferometer.

In a specific embodiment, the optical isolator is implemented as an optical coupler.

In another specific embodiment, the optical isolator is implemented as an optical circulator.

The fourth variant of the developed interferometric device, the same as another implementation of the second modification of the device known from RU Patent No. 2100787 is part of a device for optical coherence tomography. The interferometric device includes optically coupled, a source of low-coherence optical radiation, an optical interferometer, a delivering member for delivering low-coherence optical radiation to the object under study designed as an optical probe, and means for lateral scanning which is, at least partially, part of the optical probe. The optical interferometer includes at least one optical coupler, two arms, a first fiber-optic controlled scanner and a second fiber-optic controlled scanner. The optical interferometer further includes a source of AC control voltage connected with the first fiber-optic controlled scanner. The first fiber-optic controlled scanner performs a function of in-depth scanning of a coherence window of the low-coherence optical radiation within an observation range of the object under study.

In contrast to this realization of the second modification of the interferometric device known from RU Patent No. 2100787, according to the invention, in the forth variant of the developed interferometric device, the second fiber-optic controlled scanner performs a function of compensating an optical path length aberration for the low-coherence optical radiation directed towards the object under study, caused by lateral scanning. The optical interferometer further includes a source of compensating control voltage connected with the second fiber-optic controlled scanner. The source of compensating control voltage is designed such as to allow for generating a control voltage that provides compensation of a deviation of a tomographic image of a cross-section of the object under study in the presence of the aberration, from an undistorted tomographic image of the cross-section of the object under study.

In a particular embodiment, the first fiber-optic controlled scanner is implemented such as to allow for varying an optical length of a corresponding arm of the optical interferometer within at least several tens of operating wavelengths of the source of the optical radiation. The second fiber-optic controlled scanner is implemented such as to provide varying an optical length of a corresponding arm of the optical interferometer within at least several operating wavelengths of the source of optical radiation.

In a specific embodiment, the first fiber-optic controlled scanner is designed as a piezoelectric fiber-optic controlled delay line.

In another specific embodiment, the second fiber-optic controlled scanner is designed as a piezoelectric fiber-optic controlled delay line.

In another specific embodiment, the first fiber-optic controlled scanner is designed as a magnetostrictive fiber-optic controlled delay line.

In another specific embodiment, the second fiber-optic controlled scanner is designed as a magnetostrictive fiber-optic controlled delay line.

In one of the variants of the developed interferometric device the fiber-optic controlled scanner implements two functions simultaneously: a function of in-depth scanning of a coherence window of the low-coherence optical radiation within an observation range of the object under study and a function of controlling a boundary location of the of the observation range. In another modification of this variant, when the interferometric device is part of a device for optical coherence tomography and the means for lateral scanning is, at least partially, part of the optical probe, the fiber-optic controlled scanner performs, in addition, a third function: a function of compensating an optical path length aberration for the low-coherence optical radiation directed towards the object under study, caused by lateral scanning.

In another variant of the developed interferometric device, the fiber-optic controlled scanner performs a function of in-depth scanning of the coherence window of low-coherence optical radiation within the observation range of the object under study and a function of compensating the optical path length aberration of the low-coherence optical radiation directed towards the object under study, caused by lateral scanning. In the third variant of the developed interferometric device, the first fiber-optic controlled scanner, the same as in the known device, performs a function of in-depth scanning of the coherence window of the low-coherence optical radiation within the observation range of the object under study, wherein the second fiber-optic controlled scanner, in contrast to the known device, performs a function of controlling a boundary location of the observation range. Moreover, when the interferometric device is part of a device for optical coherence tomography and the means for lateral scanning is, at least partially, part of the optical probe, either the first fiber-optic controlled scanner, or the second fiber-optic controlled scanner may further perform a function of compensating the optical path length aberration for the low-coherence optical radiation directed towards the object under study, caused by lateral scanning.

In the fourth variant of the developed interferometric device, the first fiber-optic controlled scanner, the same as in the known device, performs a function of in-depth scanning of the coherence window of the low-coherence optical radiation within the observation range of the object under study, wherein the second fiber-optic controlled scanner, in contrast to the known device, performs a function of compensating an optical path length aberration for the low-coherence optical radiation directed towards the object under study, caused by lateral scanning. To perform the function of in-depth scanning of the coherence window of the low-coherence optical radiation within the observation range of the object under study, the piezoelectric controlled delay line must allow for varying the optical length of a corresponding arm of the optical interferometer within at least several tens of operating wavelengths of the source of optical radiation. To perform the function of controlling a boundary location of the observation range, the piezoelectric controlled delay line must allow for changing the optical length of a corresponding arm of the optical interferometer within at least several thousands of operating wavelengths of the source of optical radiation. To perform the function of compensating the optical path length aberration for the low-coherence optical radiation directed towards the object under study, caused by lateral scanning, the piezoelectric controlled delay line must allow for varying the optical length of a corresponding arm of the optical interferometer within at least several operating wavelengths of the source of optical radiation. It is significant, that all above functions are capable if being executed using a fiber-optic controlled scanner implemented either as a fiber-optic piezoelectric controlled delay line, or as a magnetostrictive controlled delay line, upon application of an appropriate control voltage.

In a preferred embodiment, a fiber-optic piezoelectric controlled delay line is used including a piezoelectric element characterized by a high transverse inverse piezoelectric effect, and an optical fiber attached to the piezoelectric element. The piezoelectric element is capable of having an electric field produced within it. A dimension of the piezoelectric element in a direction generally orthogonal to the electric field vector substantially exceeds a dimension of the piezoelectric element in a direction generally aligned with the electric field vector. The length of the optical fiber substantially exceeds a diameter of the piezoelectric element.

The proposed variants of the interferometric device expand the class of interferometric devices designed for examining internal structures of objects by means of optical coherence tomography, which allow for controlling a boundary location of an observation range, while simplifying operation of such devices. In addition, the proposed variants of the interferometric device expand the class of mentioned interferometric devices, which are part of devices for optical coherence tomography, that allow for correcting a distortion of the tomographic image of a cross-section of the object, which distortion is caused by aberration of the optical path length for the low-coherence optical radiation directed towards the object under study, in the process of lateral scanning. Specific types and implementations of the interferometric device as well as of its elements, in particular, the optical interferometer, the piezoelectric element, the locations of the delivering member and other elements, define the invention in its particular embodiments.

BRIEF DESCRIPTION OF DRAWINGS

FIG. 5 is one of the specific implementations of a fiber-optic piezoelectric controlled delay line, wherein FIG. 5a is a top view; and FIG. 5b is an AA section).

MODES FOR CARRYING OUT THE INVENTION

The device shown in FIG. 1 operates as follows.

A source 1 generates a low-coherence optical radiation which in a specific embodiment is capable of being of the visible or near IR wavelength range. The generated radiation then arrives at an optical interferometer 2. A semiconductor superluminescent diode, a spontaneous emission superluminescent diode based on doped optical fiber, a solid-state or fiber-optic femtosecond laser, are capable of being used as the source 1. The source 1 is capable of being implemented as a source of polarized or non-polarized optical radiation. The optical interferometer 2 is capable of being designed in accordance with any known design, for example, as a Michelson interferometer, a Mach-Zehnder interferometer, or in accordance with a hybrid design known from U.S. Pat. No. 5,291,267 and from U.S. Pat. No. 6,657,727.

Figure 1:
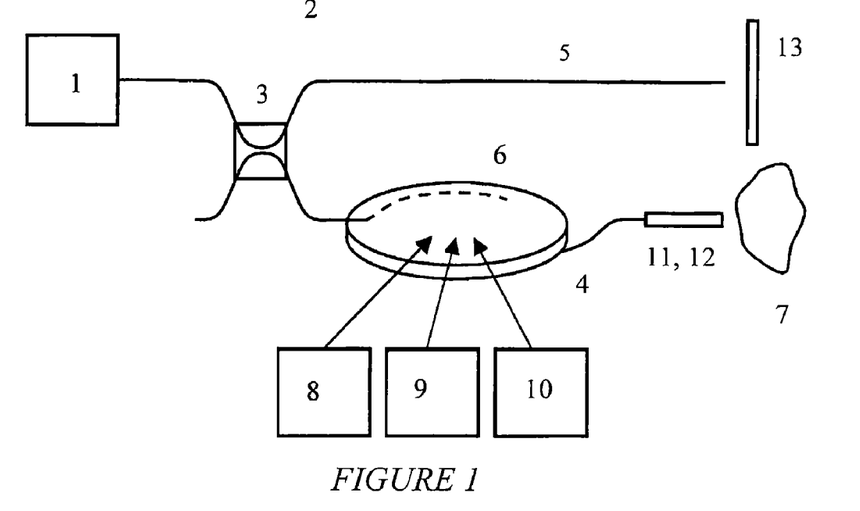
FIG. 1 is a functional layout of one embodiment of a first variant of the developed interferometric device.

In the interferometric device shown in FIG. 1, the optical interferometer 2 is implemented as a Michelson interferometer and includes an optical coupler 3 and two arms, one of which is a sampling arm 4 and the other is a reference arm 5. The optical coupler 3 splits the low-coherence optical radiation from the source 1 into two beams of low-coherence optical radiation and feeds the beams into the sampling arm 4 and the reference arm 5 of the optical interferometer 2. The optical coupler 3 is capable of being made as an optical fiber coupler. A delivering member 11, which in a specific embodiment is part of the sampling arm 4 and is designed as an optical probe 12, provides delivery of the optical radiation to an object under study 7.

The optical probe 12 may be implemented in accordance with any known design. For example, it may be an endoscope, an endoscopic probe, a catheter, a conducting catheter, a needle, or it may be implanted in a body to provide access to an internal organ. The optical probe 12 designed for acquiring circular tomographic images (e.g., a catheter for acquiring tomographic images of the internal lumens of vessels) may be attached to a residual part of the interferometer through a rotating connection. The optical probe 12 may include means for lateral scanning and may be designed, for example, as a fiber-optic probe known from RU Patent No. 2148378. The delivering member 11 also provides feeding a signal reflected or backscattered by the object under study 7 back to the sampling arm 4. A reference mirror 13 placed in the reference arm 5 reflects the low-coherence optical radiation incident onto it back into the reference arm 5. One of the arms of the optical interferometer 2, in a specific embodiment the sampling arm 4, includes a fiber-optic controlled scanner 6.

Figure 5:
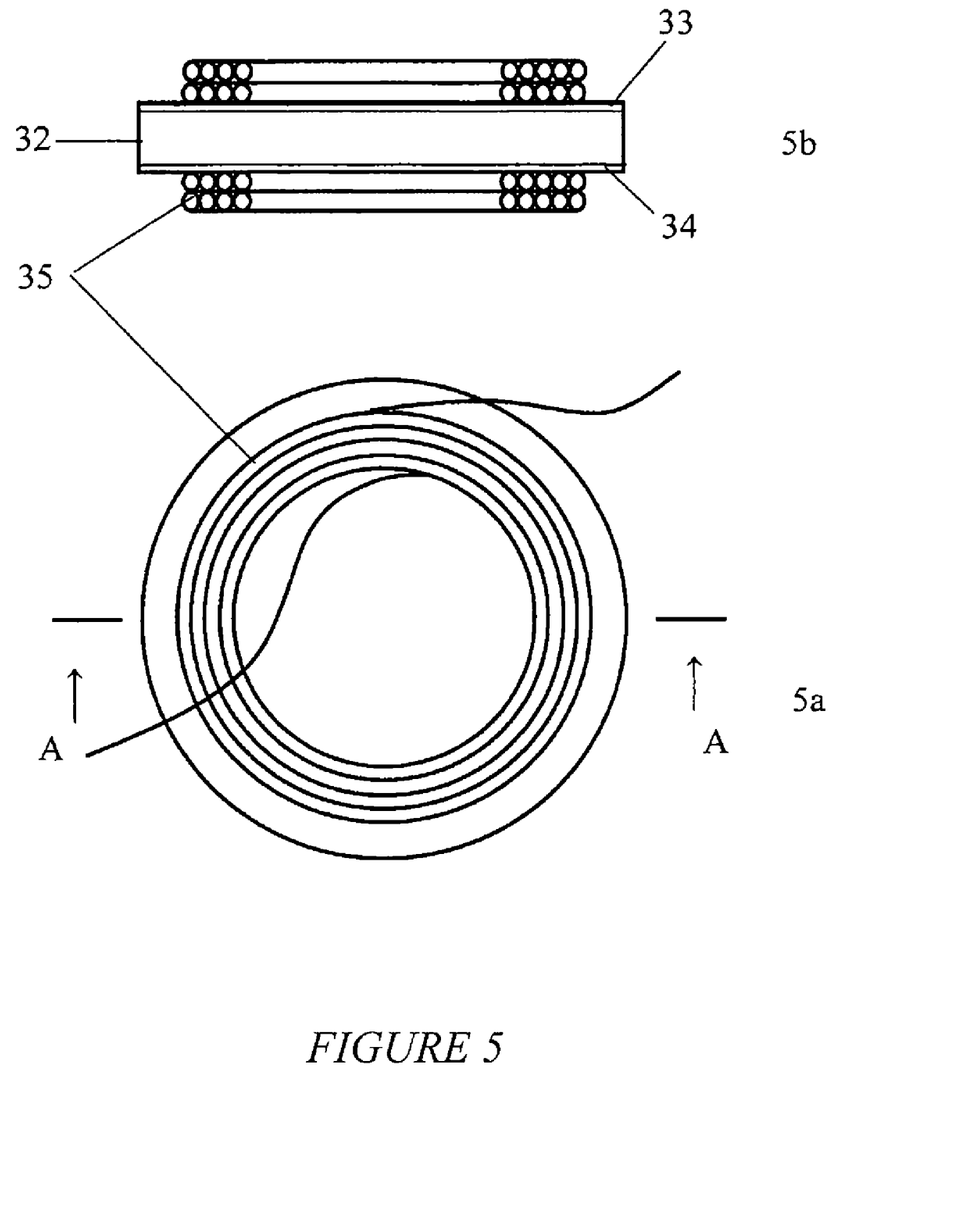

In a preferred embodiment, the fiber-optic controlled scanner 6 is designed as a fiber-optic piezoelectric controlled delay line, a layout of which is shown in FIG. 5. A fiber-optic piezoelectric controlled delay line with a cylindrical piezoelectric element produced by Canadian Instrumentation & Research, Ltd (Model 916) is also capable of being used as the fiber optic controlled scanner 6. One may also use a fiber-optic piezoelectric controlled delay line of the PZ2-HS type with a cylindrical piezoelectric element produced by OPTIPHASE, Inc (USA). The fiber-optic controlled scanner 6 may also be implemented as a magnetostrictive fiber-optic controlled delay line similar, for example, to the one described in the following paper: Trowbridge, F. R., Phillips, R. L. "Metallic-glass fiber-optic phase modulators", Optics Letters, vol. 6, 1981, p. 636-638.

The fiber-optic controlled scanner 6 under the influence of an electric charge is capable of changing the optical length of the sampling arm 4 of the optical interferometer 2 within at least several thousands of operating wavelengths of the source 1. In the interferometric device shown in FIG. 1, the fiber-optic controlled scanner 6 performs a function of controlling a boundary location of an observation range, a function of in-depth scanning of a coherence window of the low-coherence optical radiation within the observation range of the object under study, and a function of compensating an aberration of an optical path length for the low-coherence optical radiation directed towards the object under study, caused by lateral scanning. The first two mentioned functions of the fiber-optic controlled scanner 6 are implemented as follows.

A controlled source 9 of control DC voltage, connected with the fiber-optic controlled scanner 6, provides generating of a given control DC voltage. The level of the control voltage is defined by a given boundary location of the observation range. When such control voltage is applied to the fiber-optic controlled scanner 6, the optical length of the sampling arm 4 of the optical interferometer 2 changes correspondingly. This results in matching the optical lengths of the sampling arm 4 and the reference arm 5 in the range necessary for controlling a boundary location of the observation range. While a boundary location of the observation range may be controlled manually, it may also be controlled automatically, for example, as in the device known from U.S. Pat. No. 6,552,796.

A source 8 of AC control voltage is connected with the fiber-optic controlled scanner 6 and in a specific embodiment, provides generating of an AC sawtooth voltage, which is applied to the fiber-optic controlled scanner 6. The amplitude of this control voltage is determined by the parameters of the fiber optic controlled scanner 6. The control voltage applied to the fiber-optic controlled scanner 6, imparts a variation in the optical length of the sampling arm 4 of the optical interferometer 2 at a constant velocity V. Therefore a difference Δ between the optical lengths of the sampling arm 4 and the reference arm 5 of the optical interferometer 2 varies at the same velocity V according to the law of the control voltage variation. This provides in-depth scanning of the coherence window of low-coherence optical radiation within the observation range of the object under study 7.

The optical interferometer 2 provides an interference signal, which results from combining roundtrip signals from the sampling arm 4 and the reference arm 5. When the difference between the optical lengths of the arms 4 and 5 is varied by the controlled scanner 6 in accordance with the law of the control voltage, the intensity of the interference optical radiation at the output of the optical coupler 3 of the optical interferometer 2 is modulated at a Doppler frequency $f=V/\lambda$, where $$V=d\Delta/dt;$$

V is the velocity of variation in the optical length difference Δ between the sampling arm 4 and the reference arm 5 of the optical interferometer 2; and λ is the central wavelength of the source 1.

The law of the interference modulation corresponds to the variation in the intensity of optical radiation reflected or backscattered from various depths of the object under study 7.

In a specific embodiment, the interferometric device shown in FIG. 1 is part of a device for optical coherence tomography. In this embodiment, the optical probe 12 includes means for lateral scanning (not shown in the drawing), wherein the coupler 3 of the interferometer 2 is connected with at least one photodetector, the latter being connected with a processing and displaying unit (not shown in the drawing). The means for lateral scanning (not shown in the drawing) is part of the optical probe 12, and performs lateral scanning of the coherence window of the low-coherence optical radiation. The processing and displaying unit (not shown in the drawing) of the device for optical coherence tomography performs rendering of a tomographic image of a cross-section of the object under study 7 using an output signal from the photodetector (not shown in the drawing). The signal at the photodetector output is proportional to the interference modulation of the intensity of the combined optical radiation at the output of the optical coupler 3.

The fiber-optic controlled scanner 6 provides compensation of the aberration of the optical path length for the low-coherence optical radiation directed towards the object under study 7, caused by lateral scanning, in the following manner. A source 10 of compensating control voltage connected with the fiber-optic controlled scanner 6, generates a control voltage, which is applied to the fiber-optic controlled scanner 6. The compensating control voltage generated by the source 10, to a first approximation is proportional to a deviation of a tomographic image of a cross-section of the object under study 7 in the presence of the aberration, from an undistorted tomographic image of the cross-section of the object under study 7, and is inversely proportional to the coefficient of sensitivity of the fiber-optic controlled scanner 6. The compensating control voltage varies synchronously with a lateral scanning coordinate. Synchronization in the device is capable of being provided either by software or by appropriate synchronizing elements and feedback (not shown in the drawing). The shape of the compensating voltage generated by the source 10 may be determined either computationally or experimentally in the course of calibration of the interferometric device. In most cases, for an object under study with a flat surface, the compensating voltage shape is capable of being approximated by a polynomial function, for instance, by a second-order parabolic curve. In the absence of compensation, lateral scanning of a flat object under study with a lateral amplitude of 1 mm, typically yields a maximum deviation value of ~200 μm of the tomographic image of the cross-section of the object under study, from a respective flat tomographic image. The coefficient of sensitivity for the fiber-optic controlled scanner 6 in a preferred embodiment of the developed interferometric device, is ~10 μm/V. Thus, such deviation may be compensated by applying a voltage of 20V. Hence, when the control voltage is applied to the fiber-optic controlled scanner 6, the difference in the optical lengths of the arms 4 and 5 changes correspondingly, and thereby compensates the aberration resulting from the lateral scanning. Therefore, the processing and displaying unit of the device for optical coherence tomography renders an undistorted tomographic image of the cross-section of the object under study 7.

The sources 8, 9 and 10 are capable of being combined in one source of control voltage providing generation of corresponding control voltages.

The interferometric device shown in FIG. 2 operates as follows.

A source 1 generates a low-coherence optical radiation which in a specific embodiment may be of the visible or near IR wavelength range. The generated radiation is transported to a delivering member 11 through an optical isolator 20. In a specific embodiment shown in FIG. 2, the delivering member 11 is designed as an optical probe 12 and is placed outside an optical interferometer 14 of the interferometric device. The optical isolator 20 may be implemented as an optical coupler similar to the optical coupler 3, or as an optical circulator. The optical probe 12 provides delivery of the optical radiation to an object under study 7.

A distal part of the delivering member 11 together with an object under study 7 forms an additional optical interferometer 21. In a specific embodiment, the additional optical interferometer 21 is formed by a tip of the optical probe 12 and the object under study 7. The delivering member 11 is also optically coupled with the optical interferometer 14 through the optical isolator 20. The optical interferometer 14 is capable of being implemented in accordance with any known design, for example, as a Michelson interferometer, a Mach-Zehnder interferometer, or in accordance with a hybrid design, known, for example, from U.S. Pat. No. 5,291,267 and from U.S. Pat. No. 6,657,727.

Figure 2:
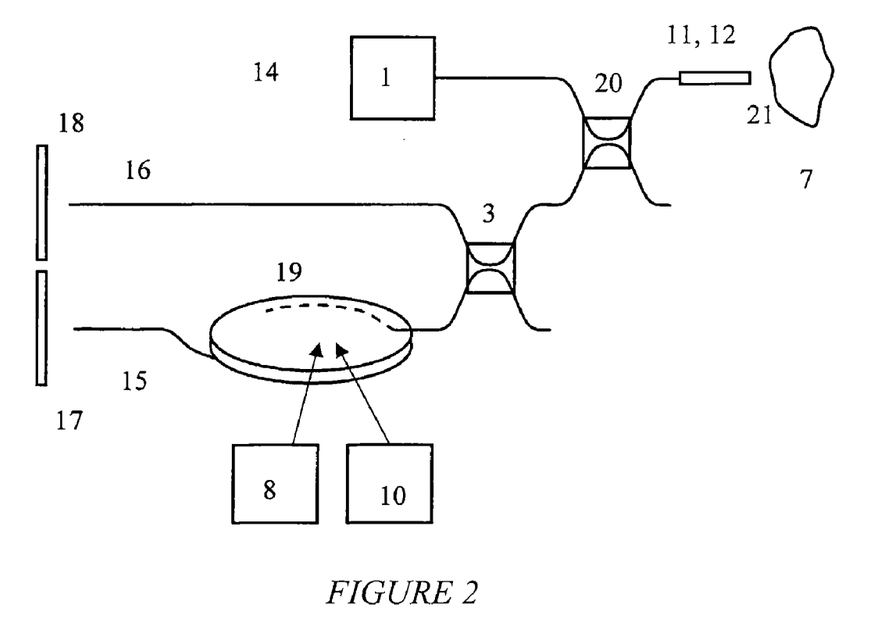
FIG. 2 is a functional layout of one embodiment of a second variant of the developed interferometric device.

In a specific embodiment shown in FIG. 2, the optical interferometer 14 is designed as a Michelson interferometer and includes an optical coupler 3, a first arm 15 and a second arm 16. A mirror 17 is placed at the end of the first arm 15 and a mirror 18 is placed at the end of the second arm 16. The mirrors 17 and 18 are capable of being implemented as Faraday mirrors. Optical radiation reflected from the tip of the optical probe 12 and optical radiation reflected or backscattered by the object under study 7, returns to the optical interferometer 14 through the optical isolator 20 and the optical coupler 3. One of the arms of the optical interferometer 14, which in a specific embodiment is the first arm 15, includes a fiber-optic controlled scanner 19. The fiber-optic controlled scanner 19 performs a function of in-depth scanning of a coherence window of the low-coherence optical radiation within an observation range of the object under study 7. The fiber-optic controlled scanner 19 also performs a function of compensating an aberration of an optical path length for the low-coherence optical radiation directed towards the object under study 7, caused by lateral scanning.

The optical interferometer 14 also includes a source 8 of AC control voltage and a source 10 of compensating control voltage, which are both connected with the fiber-optic controlled scanner 19. The fiber-optic controlled scanner 19 is implemented as a fiber-optic piezoelectric controlled delay line such as to provide varying the optical length of a corresponding arm of the optical interferometer 14, in a specific implementation the optical length of the first arm 15, within at least several tens of operating wavelengths of the source 1. From a design standpoint, the fiber-optic controlled scanner 19 may be built analogous to the fiber-optic controlled scanner 6. The AC control voltage from the source 8 applied to the fiber-optic controlled scanner 19, leads to varying the optical length of the first arm 15 of the optical interferometer 14 at a constant velocity V. Hence it leads to varying a difference Δ between the optical lengths of the first arm 15 and the second arm 16 of the optical interferometer 14, in accordance with the variation law of the control voltage.

This provides in-depth scanning of the coherence window of the low-coherence optical radiation within the observation range of the object under study 7. A control of a boundary location of the observation range is not provided by this variant of the interferometric device.

The optical interferometer 14 together with the additional optical interferometer 21 produce an interference signal resulting from combing roundtrip signals from the first arm 15 and the second arm 16. When the difference between the optical lengths of the arms 15 and 16 is varied by the controlled scanner 19 in accordance with the law of the control voltage from the source 8, the intensity of the combined optical radiation at the output of the optical coupler 3 of the optical interferometer 14 becomes modulated at a Doppler frequency f=V/λ, where $V=d\Delta/dt;$ V is the velocity of variation in the optical length difference Δ between the first and the second arms 15 and 16, respectively, of the optical interferometer 14; and λ is the central wavelength of the source 1.

The law of the interference modulation corresponds to the variation in the intensity of the optical radiation reflected or backscattered from various depths of the object under study 7

In a specific embodiment, the interferometric device shown in FIG. 2 is part of a device for optical coherence tomography. In this embodiment, the optical probe 12 includes means for lateral scanning (not shown in the drawing) which performs lateral scanning of the low-coherence optical radiation. A processing and displaying unit (not shown in the drawing) of the device for optical coherence tomography performs rendering of a tomographic image of a cross-section of the object under study 7 using an output signal from a photodetector (not shown in the drawing). The optical coupler 3 of the interferometer 14 is connected with at least one photodetector which is further connected with the processing and displaying unit (not shown in the drawing). The signal at the photodetector output is proportional to the interference modulation of the intensity of the combined optical radiation at the output of the optical coupler 3.

The source 10 generates a compensating control voltage similar to that generated in the interferometric device shown in FIG. 1, which is applied to the fiber-optic controlled scanner 19. Application of this control voltage to the fiber-optic controlled scanner 19 leads to a corresponding varying in the optical length difference between the arms 15 and 16. The latter thereby compensates the aberration occurring as a result of lateral scanning in a manner similar to that realized in the interferometric device shown in FIG. 1. Therefore, a processing and displaying unit of the device for optical coherence tomography renders an undistorted tomographic image of a cross-section of the object under study 7.

The sources 8 and 10 are capable of being combined in one source of control voltage providing generation of corresponding control voltages.

Figure 3:
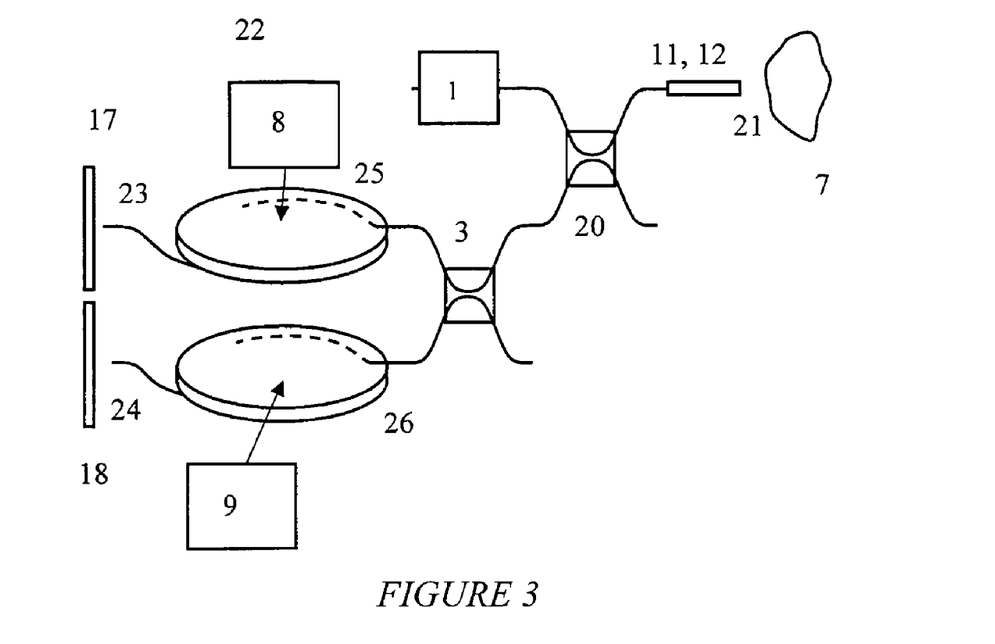
FIG. 3 is a functional layout of one embodiment of a third variant of the developed interferometric device.

The interferometric device shown in FIG. 3 includes an optical interferometer 22 and operates analogous to the interferometric device shown in FIG. 2. The optical interferometer 22 may be implemented in a similar manner to the optical interferometer 14 of the interferometric device shown in FIG. 2. The only difference is that in-depth scanning of the coherence window of the low-coherence optical radiation within the observation range of the object under study 7 is performed by a fiber-optic controlled scanner 25, wherein the control of a boundary location of the observation range is performed by a fiber-optic controlled scanner 26. The fiber-optic controlled scanner 25 is placed in a first arm 23 of the optical interferometer 22, and the fiber-optic controlled scanner 26 is placed in a second arm 24 of the optical interferometer 22.

A source 8 of an AC control voltage is connected with the fiber-optic controlled scanner 25, while a source 9 of a DC control voltage is connected with the fiber-optic controlled scanner 26. The fiber-optic controlled scanner 25 provides varying of the optical length of the first arm 23 of the optical interferometer 22 within at least several tens of operating wavelengths of the source 1. The fiber-optic controlled scanner 26 provides a change in the optical length of the second arm 24 of the optical interferometer 22 within at least several thousands of operating wavelengths of the source 1. From a design standpoint, the fiber-optic controlled scanners 25 and 26 may be designed in a similar manner to the fiber-optic controlled scanners 6 and 19. In the interferometric device shown in FIG. 3, the same as in the device shown in FIG. 2, the delivering member 11 is implemented as an optical probe 12 and is placed outside the optical interferometer 22 of the interferometric device.

The particular embodiment shown in FIG. 3, does not provide distortion correction of the tomographic image of a cross-section of the object under study, which distortion is due to an aberration of the optical path length for the low-coherence optical radiation directed towards the object under study 7, caused by lateral scanning. However, the interferometric device shown in FIG. 3 is capable of being part of a device for optical coherence tomography. In this embodiment, the interferometric device includes means for lateral scanning (not shown in the drawing), which is, at least partially, part of the optical probe 12. In such an embodiment, one of the fiber-optic controlled scanners, either the fiber-optic controlled scanner 25, or the fiber-optic controlled scanner 26, upon application of appropriate control voltage may further perform a function of compensating an optical path length aberration for the low-coherence optical radiation directed towards the object under study 7, caused by lateral scanning. For employing this option, the interferometric device further includes a source 10 of compensating control voltage connected with a corresponding fiber-optic controlled scanner (not shown in the drawing).

Figure 4:
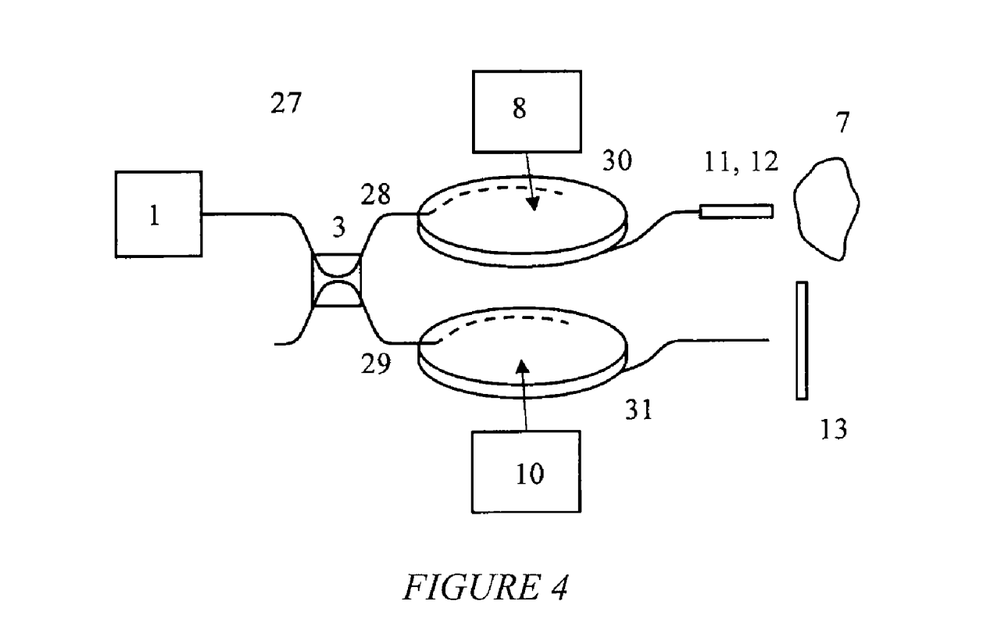
FIG. 4 is a functional layout of one embodiment of a forth variant of the developed interferometric device.

The interferometric device shown in FIG. 4 operates analogous to the interferometric device shown in FIG. 1. An optical interferometer 27 may be designed in a similar manner to the optical interferometer 2 of the interferometric device shown in FIG. 1. The only difference is that in-depth scanning of the coherence window of the low-coherence optical radiation within the observation range of the object under study 7 is performed by a fiber-optic controlled scanner 30, wherein compensation of the optical path length aberration for the low-coherence optical radiation directed towards the object under study 7, caused by lateral scanning, is performed by a fiber-optic controlled scanner 31. The fiber-optic controlled scanner 30 is placed in a sampling arm 28 of the optical interferometer 27, and the fiber-optic controlled scanner 31 is placed in a reference arm 29 of the optical interferometer 27. A source 8 of an AC control voltage is connected with the fiber-optic controlled scanner 30, wherein a source 10 of compensating control voltage is connected with the fiber-optic controlled scanner 31. The fiber-optic controlled scanner 30 provides varying of the optical length of the sampling arm 28 of the optical interferometer 27 within at least several tens of operating wavelengths of the source 1. The fiber-optic controlled scanner 31 provides varying of the optical length of the reference arm 29 of the optical interferometer 27 within at least several operating wavelengths of the source 1. From a design standpoint, the fiber-optic controlled scanners 30 and 31 may be designed in a similar manner to the fiber-optic controlled scanners 6, 19, 25, and 26.

In a particular embodiment shown in FIG. 4, the same as in the device shown in FIG. 1, the delivering member 11 is part of one of the arms of the interferometer 27, namely, part of the sampling arm 28. In this embodiment, the delivering member 11 is designed as an optical probe 12. The interferometric device shown in FIG. 4 is part of a device for optical coherence tomography. The optical probe 12 includes means for lateral scanning (not shown in the drawing), wherein the optical coupler 3 is connected with, at least, one photodetector connected with a processing and displaying unit (not shown in the drawing).

The particular embodiment shown in FIG. 4, does not involve a control of a boundary location of the observation range.

All the embodiments of the developed interferometric device, when used as part of a device for optical coherence tomography, may use a photodiode as a photodetector in the optical coherence tomography device. The processing and displaying unit may be implemented, for example, analogous to that described in the paper by V. M. Gelikonov et al. "Optical coherence tomography of microinhomogeneities of biological tissues" Letters to the Journal of Experimental and Theoretical Physics, vol. 61, issue 2, pages 149-153. Such processing and displaying unit includes a band-pass filter, a logarithmic amplifier, an amplitude detector, an analog-digital converter and a computer connected in series. The means for lateral scanning may be implemented in accordance with any known design, such as, for example, known from U.S. Pat. Nos. 3,470,320; 5,317,148; and 5,321,501. In a preferred embodiment of the invention, the means for lateral scanning is designed according to RU Patent No. 2148378.

The fiber-optic piezoelectric controlled delay line schematically shown in FIG. 5, includes a piezoelectric element characterized by a high transverse inverse piezoelectric effect. The piezoelectric element is implemented such that an electric field is capable of being generated within it. A dimension of the piezoelectric element in a direction generally orthogonal to the electric field vector substantially exceeds a dimension of the piezoelectric element in a direction generally aligned with the electric field vector. The fiber-optic piezoelectric controlled delay line shown in FIG. 5 operates as follows.

A control voltage from a source of control voltage (not show in FIG. 5) is applied to electrodes 33 and 34 which are attached to opposite surfaces of the piezoelectric element.

The piezoelectric element in a particular embodiment is designed as a piezoelectric plate 32. An optical fiber 35 is attached to the same surfaces of the piezoelectric plate 32. The piezoelectric plate 32 is made of a piezoelectric material characterized by a high transverse inverse piezoelectric effect; for example, of CTBS-1 or PZT-5H type. The electrodes 33 and 34 are made of metal, for example, of silver. The ratio of the diameter of the piezoelectric plate 32 to its thickness is determined by a provision for the piezoelectric element to provide a requested change in the length of the optical fiber 35, taking into account a specific laying configuration of the optical fiber 35.

The length of the optical fiber 35 substantially exceeds the diameter of the piezoelectric plate 32. In a specific implementation of the piezoelectric fiber-optic controlled delay line shown in FIG. 5, the optical fiber 35 is laid spirally. The spiral laying may have multiple layers, wherein FIG. 5 illustrates a two-layer spiral laying of the optical fiber 35. Both isotropic and polarization maintaining optical fiber is capable of being used in the interferometric device, as the optical fiber 35. Application of a control voltage to the electrodes 33 and 34 produces potential difference $\phi_1$ between the surfaces of piezoelectric plate 32, which induces a transverse inverse piezoelectric effect in the piezoelectric plate 32. The absolute value of the change in the diameter of the piezoelectric plate 32 $|\Delta D|$ may be expressed as follows:

$$|\Delta D| = (D/h) * d_{31} * \phi_1$$

where h is the thickness of the piezoelectric plate 32; and $d_{31}$ is the piezoelectric modulus.

The change in a diameter D of the piezoelectric plate 32 follows the law of the control voltage variation and results in a corresponding stretching or contraction of the optical fiber 35 attached to the surfaces of the piezoelectric plate 32. The change in the length of the optical fiber 35 depends, among other factors, on the type of the optical fiber laying.

In accordance with the above expression, a single-layered double-sided spiral laying of 24 meters of the optical fiber 35 attached to the surfaces of the piezoelectric plate 32 with a diameter of 65 mm, with a control voltage of an amplitude of 275 V, is capable of yielding a 2 mm change in the length of the optical fiber 35, for a piezoelectric material of CTBS-1 type; and a 2.4 mm change for a piezoelectric material of PZT-5H type. For a similar plate, using the same control voltage but for five layers of the optical fiber 35 with a total length of 120 m, a 10 mm change in the length of the optical fiber 35 for a piezoelectric material of CTBS-1 type is capable of being obtained; and a 12 mm change for a piezoelectric material of PZT-5H type. The experimental data is given for roundtrip paths of optical radiation in a Michelson optical interferometer.

Thus, when appropriate control voltage is applied to the fiber-optic piezoelectric controlled delay line having a laying of sufficient amount of optical fiber, then such a fiber-optic piezoelectric controlled delay line as shown schematically in FIG. 5, is capable of performing a function of in-depth scanning of the coherence window of the low-coherence optical radiation within the observation range of the object under study, a function of controlling a boundary location of the observation range, and a function of compensating the optical path length aberration for the low-coherence optical radiation directed towards the object under study, caused by lateral scanning.

INDUSTRIAL APPLICABILITY

The invention is capable of being employed in devices for examining the internal structures of objects by optical methods, namely in low-coherence reflectometers and optical coherence tomography devices which are used, in particular, for medical diagnostics of conditions of individual organs and systems of a human body, including, in vivo examinations, and for technical diagnostics, e.g., for monitoring technological processes. It should be noted that the invention is capable of being implemented using standard means.

What is claimed is:

1. An interferometric device specified by an observation range of an associated object under study, the observation range having a boundary, comprising:
    a source of low-coherence optical radiation having an operating wavelength, the low-coherence optical radiation specified by a coherence window;
    an optical interferometer optically coupled with the source of low-coherence optical radiation, the optical interferometer comprising
        at least one optical coupler,
        two arms,
        a first fiber-optic controlled scanner placed in one of the arms of the optical interferometer for performing a function of in-depth scanning of the coherence window of the low-coherence optical radiation within the observation range of the object under study, and
        a source of AC control voltage connected with the fiber-optic controlled scanner; and
    a delivering member for delivering low-coherence optical radiation to an associated object under study optically coupled with the source of low-coherence optical radiation and with the optical interferometer;
    wherein the optical interferometer further comprises a source of DC control voltage connected with the fiber-optic controlled scanner; and
    wherein the first fiber-optic controlled scanner further performs a function of controlling a boundary location of the observation range.

2. The interferometric device of claim 1 wherein the delivering member for delivering low-coherence optical radiation to an associated object under study, is designed as an optical probe.

3. The interferometric device of claim 2:
    wherein the interferometric device is part of a device for optical coherence tomography and includes means for lateral scanning;
    wherein the means for lateral scanning is, at least partially, part of the optical probe;
    wherein the first fiber-optic controlled scanner further performs a function of compensating an optical path length aberration for the low-coherence optical radiation directed towards an associated object under study, caused by lateral scanning;
    wherein the first fiber-optic controlled scanner is implemented such as to allow for changing an optical length of a corresponding arm of the optical interferometer within at least several thousands of operating wavelengths of the source of optical radiation;
    wherein the optical interferometer further comprises a source of compensating control voltage connected with the first fiber-optic controlled scanner; and
    wherein the source of compensating control voltage is implemented such as to allow for generating a control voltage that provides compensation of a deviation of a tomographic image of a cross-section of an associated object under study in the presence of the aberration, from an undistorted tomographic image of the cross-section of an associated object under study.

4. The interferometric device of claim 2:
wherein the interferometric device is part of a device for optical coherence tomography and includes means for lateral scanning;
wherein the means for lateral scanning is, at least partially, part of the optical probe;
wherein the optical interferometer further comprises a second fiber-optic controlled scanner, which is placed in one of the arms of the optical interferometer and performs a function of compensating an optical path length aberration for the low-coherence optical radiation directed towards an associated object under study, caused by lateral scanning;
wherein the optical interferometer further comprises a source of compensating control voltage connected with the second fiber-optic controlled scanner;
wherein the source of compensating control voltage is implemented such as to allow for generating a control voltage that provides compensation of a deviation of a tomographic image of a cross-section of an associated object under study in the presence of the aberration, from an undistorted tomographic image of the cross-section of an associated object under study;
wherein the first fiber-optic controlled scanner is implemented such as to allow for changing an optical length of a corresponding arm of the optical interferometer within at least several thousands of operating wavelengths of the source of optical radiation; and
wherein the second fiber-optic controlled scanner is implemented such as to allow for changing an optical length of a corresponding arm of the optical interferometer within at least several operating wavelengths of the source of optical radiation.

5. The interferometric device of claim 4 wherein at least one of the first fiber-optic controlled scanner, and the second fiber-optic controlled scanner, is designed as a piezoelectric fiber-optic controlled delay line.

6. The interferometric device of claim 1 wherein the first fiber-optic controlled scanner is designed as a piezoelectric fiber-optic controlled delay line.

7. The interferometric device of claim 6:
wherein the fiber-optic piezoelectric controlled delay line comprises:
a piezoelectric element having a diameter and characterized by a high transverse inverse piezoelectric effect, and
an optical fiber attached to the piezoelectric element, the optical fiber having a length;
wherein the piezoelectric element is capable of having an electric field produced within it;
wherein a dimension of the piezoelectric element in a direction substantially orthogonal to the electric field vector substantially exceeds a dimension of the piezoelectric element in a direction substantially aligned with the electric field vector; and
wherein the length of the optical fiber substantially exceeds the diameter of the piezoelectric element.

8. The interferometric device of claim 1 wherein the first fiber-optic controlled scanner is designed as a magnetostrictive fiber-optic controlled delay line.

9. The interferometric device of claim 1 wherein the delivering member for delivering low-coherence optical radiation to an associated object under study is part of one of the arms of the optical interferometer.

10. The interferometric device of claim 1:
wherein the delivering member for delivering low-coherence optical radiation to an associated object under study is placed outside of the optical interferometer and is optically coupled to it through an optical isolator; and
wherein a distal part of the delivering member for delivering low-coherence optical radiation to an associated object under study together with an associated object under study, form an additional optical interferometer.

11. An interferometric device, which is part of a device for optical coherence tomography and is specified by an observation range of an associated object under study, the observation range having a boundary, comprising:
a source of low-coherence optical radiation having an operating wavelength, the low-coherence optical radiation specified by a coherence window;
an optical interferometer optically coupled with the source of low-coherence optical radiation, the optical interferometer comprising
at least one optical coupler,
two arms,
a fiber-optic controlled scanner placed in one of the arms of the optical interferometer for performing a function of in-depth scanning of the coherence window of the low-coherence optical radiation within the observation range of an associated object under study, and
a source of AC control voltage connected with the fiber-optic controlled scanner;
a delivering member for delivering low-coherence optical radiation to an associated object under study optically coupled with the source of low-coherence optical radiation and with the optical interferometer, the delivering member for delivering low-coherence optical radiation to an associated object under study being designed as an optical probe; and
means for lateral scanning, which is, at least partially, part of the optical probe;
wherein the fiber-optic controlled scanner further performs a function of compensating an optical path length aberration for the low-coherence optical radiation directed towards an associated object under study, caused by lateral scanning;
wherein the fiber-optic controlled scanner is designed such as to allow for varying an optical length of a corresponding arm of the optical interferometer within at least several tens of operating wavelengths of the source of optical radiation; and
wherein the optical interferometer further comprises a source of compensating control voltage connected with the fiber-optic controlled scanner, the source of compensating control voltage being designed such as to generate a control voltage that provides compensation of a deviation of a tomographic image of a cross-section of an associated object under study in the presence of the aberration, from an undistorted tomographic image of the cross-section of an associated object under study.

12. The interferometric device of claim 11 wherein the fiber-optic controlled scanner is designed as a piezoelectric fiber-optic controlled delay line.

13. The interferometric device of claim 12:
wherein the fiber-optic piezoelectric controlled delay line comprises:
a piezoelectric element having a diameter and characterized by a high transverse inverse piezoelectric effect, and
an optical fiber attached to the piezoelectric element, the optical fiber having a length;
wherein the piezoelectric element is capable of having an electric field produced within it;

wherein a dimension of the piezoelectric element in a direction substantially orthogonal to the electric field vector substantially exceeds a dimension of the piezoelectric element in a direction substantially aligned with the electric field vector; and wherein the length of the optical fiber substantially exceeds the diameter of the piezoelectric element.

14. The interferometric device of claim 11 wherein the fiber-optic controlled scanner is designed as a magnetostrictive fiber-optic controlled delay line.

15. An interferometric device specified by an observation range of an associated object under study, the observation range having a boundary, comprising:
a source of low-coherence optical radiation having an operating wavelength, the low-coherence optical radiation specified by a coherence window;
an optical interferometer optically coupled with the source of low-coherence optical radiation, the optical interferometer comprising
at least one optical coupler,
two arms,
a first fiber-optic controlled scanner and a second fiber-optic controlled scanner placed in corresponding arms of the optical interferometer,
a source of AC control voltage connected with the first fiber-optic controlled scanner; and
a source of DC control voltage connected with the second fiber-optic controlled scanner; and
a delivering member for delivering low-coherence optical radiation to an associated object under study optically coupled with the source of low-coherence optical radiation and with the optical interferometer;
wherein the first fiber-optic controlled scanner performs a function of in-depth scanning of the coherence window of the low-coherence optical radiation within the observation range of the object under study;
wherein the first fiber-optic controlled scanner is implemented such as to allow for varying an optical length of a corresponding arm of the optical interferometer within at least several tens of operating wavelengths of a source of the optical radiation;
wherein the second fiber-optic controlled scanner performs a function of controlling a boundary location of the observation range; and
wherein the second fiber-optic controlled scanner is implemented such as to allow for changing the optical length of a corresponding arm of the optical interferometer within at least several thousands of operating wavelengths of a source of the optical radiation.

16. The interferometric device of claim 15:
wherein the delivering member for delivering low-coherence optical radiation to an associated object under study, is designed as an optical probe;
wherein the interferometric device is part of a device for optical coherence tomography and includes means for lateral scanning;
wherein the means for lateral scanning is, at least partially, part of the optical probe;
wherein at least one of the first fiber-optic controlled scanner, and the second fiber-optic controlled scanner further performs a function of compensating an optical path length aberration for the low-coherence optical radiation directed towards an associated object under study, caused by lateral scanning;
wherein the optical interferometer further comprises a source of compensating control voltage connected with at least one of the first fiber-optic controlled scanner, and the second fiber-optic controlled scanner; and wherein the source of compensating control voltage is implemented such as to allow for generating a control voltage that provides compensation of a deviation of a tomographic image of a cross-section of an associated object under study in the presence of the aberration, from an undistorted tomographic image of the cross-section of an associated object under study.

17. The interferometric device of claim 15 wherein at least one of the first fiber-optic controlled scanner, and the second fiber-optic controlled scanner, is designed as a piezoelectric fiber-optic controlled delay line.

18. The interferometric device of claim 15 wherein at least one of the first fiber-optic controlled scanner, and the second fiber-optic controlled scanner, is designed as a magnetostrictive fiber-optic controlled delay line.

19. An interferometric device, which is part of a device for optical coherence tomography and is specified by an observation range of an associated object under study, the observation range having a boundary, comprising:
a source of low-coherence optical radiation having an operating wavelength, the low-coherence optical radiation specified by a coherence window;
an optical interferometer optically coupled with the source of low-coherence optical radiation, the optical interferometer comprising
at least one optical coupler,
two arms,
a first fiber-optic controlled scanner and a second fiber-optic controlled scanner placed in corresponding arms of the optical interferometer,
a source of AC control voltage connected with the first fiber-optic controlled scanner; and
a source of compensating control voltage connected with the second fiber-optic controlled scanner; and
a delivering member for delivering low-coherence optical radiation to an associated object under study optically coupled with the source of low-coherence optical radiation and with the optical interferometer;
wherein the first fiber-optic controlled scanner performs a function of in-depth scanning of the coherence window of the low-coherence optical radiation within the observation range of the object under study;
wherein the second fiber-optic controlled scanner performs a function of compensating an optical path length aberration for the low-coherence optical radiation directed towards the object under study, caused by lateral scanning; and
wherein the source of compensating control voltage is designed such as to allow for generating a control voltage that provides compensation of a deviation of a tomographic image of a cross-section of an associated object under study in the presence of the aberration, from an undistorted tomographic image of the cross-section of an associated object under study.

20. The interferometric device of claim 19 wherein the delivering member for delivering low-coherence optical radiation to an associated object under study is part of one of the arms of the optical interferometer.

21. The interferometric device of claim 19 wherein the delivering member for delivering low-coherence optical radiation to an associated object under study is placed outside of the optical interferometer and is optically coupled with the optical interferometer through an optical isolator, wherein a distal part of the delivering member for delivering low-coherence optical radiation to an associated object under study together with an associated object under study form an additional interferometer.

* * * * *